United States Patent
Shimura (10) Patent No.: US 8,921,798 B2
(45) Date of Patent: Dec. 30, 2014

(54) DEFECT INSPECTION APPARATUS AND DEFECT INSPECTION METHOD

(71) Applicant: Hitachi High-Technologies Corporation, Tokyo (JP)

(72) Inventor: Kei Shimura, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/789,156

(22) Filed: Mar. 7, 2013

(65) Prior Publication Data

US 2014/0042332 A1    Feb. 13, 2014

(30) Foreign Application Priority Data

Aug. 10, 2012    (JP) .................................. 2012-177689

(51) Int. Cl.
  *G01J 1/42* (2006.01)
  *G01N 21/95* (2006.01)
  *G01N 21/956* (2006.01)

(52) U.S. Cl.
  CPC ............ *G01N 21/95* (2013.01); *G01N 21/9501* (2013.01); *G01N 21/95684* (2013.01)
  USPC ........................................................ 250/372

(58) Field of Classification Search
  CPC ............................................. G02F 2001/3507
  USPC ........................................................ 250/372
  See application file for complete search history.

(56) References Cited

U.S. PATENT DOCUMENTS

| | | | |
|---|---|---|---|
| 5,257,202 A | 10/1993 | Feddersen et al. | |
| 5,463,459 A | 10/1995 | Morioka | |
| 5,912,997 A * | 6/1999 | Bischel et al. | 385/15 |
| 6,005,965 A * | 12/1999 | Tsuda et al. | 382/145 |
| 6,373,565 B1 | 4/2002 | Kafka et al. | |
| 7,003,005 B1 * | 2/2006 | Lai et al. | 372/30 |
| 7,266,137 B2 * | 9/2007 | Albrecht et al. | 372/59 |
| 7,684,039 B2 * | 3/2010 | Adel et al. | 356/401 |
| 2002/0191171 A1 * | 12/2002 | Nishi | 355/67 |
| 2003/0089685 A1 * | 5/2003 | Ando | 219/121.12 |
| 2004/0218262 A1 * | 11/2004 | Chuang et al. | 359/366 |
| 2006/0132931 A1 * | 6/2006 | Epple et al. | 359/726 |
| 2008/0219702 A1 | 9/2008 | Tsukamoto et al. | |
| 2010/0187405 A1 * | 7/2010 | Arao et al. | 250/208.2 |

FOREIGN PATENT DOCUMENTS

| | | |
|---|---|---|
| JP | 11-45842 A | 2/1999 |
| JP | 2000-105203 A | 4/2000 |
| JP | 2003-194739 A | 7/2003 |
| JP | 2004-271498 A | 9/2004 |
| JP | 2007-142052 A | 6/2007 |
| JP | 2008-216790 A | 9/2008 |
| JP | 2011-171521 | 9/2011 |

\* cited by examiner

*Primary Examiner* — Kiho Kim
(74) *Attorney, Agent, or Firm* — Crowell & Moring LLP (57) ABSTRACT

Method for realizing an inspection with short wavelength, high power light source and large numerical aperture, high performance optics to improve defect inspection sensitivity is disclosed. Short wavelength high power laser is realized by using a pulse oscillation type laser suitable for generation of high output power in a short-wavelength region, In addition, a spectral bandwidth of the laser is narrowed down so that amount of chromatic aberration of detection optics with single glass material (i.e. without compensation of chromatic aberration) is lowered to permissible level. Using highly workable glass material to construct the detection optics enables necessary surface accuracy or profile irregularity conditions to be met, even if the number of lenses is increased for large NA or the lens doesn't have a rotationally symmetrical aperture.

7 Claims, 9 Drawing Sheets

SIDE VIEW

FIG. 8B

FRONT VIEW

FIG. 8C

APERTURE SHAPE OF LENS 411 OR 511

DEFECT INSPECTION APPARATUS AND DEFECT INSPECTION METHOD

BACKGROUND OF THE INVENTION

1. Field of the Invention

The present invention relates to a defect inspection apparatus and a method for inspecting an occurrence status of dust, dirt, other foreign matter, and surface defects such as pattern defects, when patterns are formed on the substrate and necessary components are fabricated thereon. Such fabrication processes include manufacturing processes for semiconductors, flat-panel displays such as liquid-crystal display elements, printed circuit substrates, or the like.

2. Description of the Related Art

In semiconductor-manufacturing processes, defects in pattern shape occur due to the presence of dust, dirt, and other foreign substances (hereinafter, referred to collectively as contamination) on the surface of a semiconductor substrate (wafer), and/or due to improper formation of electrical interconnection patterns. Such defects will cause improper electrical insulation of interconnections, short-circuiting, increased interconnection resistance, disconnections, improper insulation of capacitors, damage to a gate oxide film, or other defects. Contamination that sticks to semiconductor substrates occurs in various forms for a variety of reasons. For example, contamination may arise from a movable section of a transport device, from the human body, from the production of reactants in a processing apparatus due to process gas usage, or from chemicals or materials. Defects in pattern shape result from changes in process conditions during various steps of the pattern-forming process, including exposure to light, photographic processing, etching, cleaning, and so forth. In addition, during manufacturing processes for a flat-panel display such as a liquid-crystal display element, the display element may or will be unusable if pattern contamination arises or any form of pattern defect occurs during the pattern-forming process. Furthermore, the same also occurs during the manufacture of printed circuit substrates, and contamination and the abnormality of the process cause the short-circuiting, insufficient electrical contact, or disconnection of the patterns.

Techniques for detecting contamination and pattern defects on a semiconductor substrate are disclosed in JP-2000-105203-A, JP-2008-216790-A, U.S. Pat. No. 6,373,565. These existing methods are used to detect defects and contamination not having repeatability, by irradiating an upper surface of the semiconductor substrate (wafer) with laser light and after removing with a spatial filter the light exiting an repetitive pattern on the wafer, enhancing edges of the defects and contamination. JP-2000-105203-A also discloses a defect inspection apparatus that detects defects and contamination by emitting illumination light in a direction 45 degrees inclined with respect to a direction of a major rectilinear group of circuit patterns formed on the surface of the wafer, and thereby permitting no 0th-order diffracted light from the major rectilinear group to enter an aperture of an objective lens. JP-2000-105203A additionally discloses a defect inspection apparatus using a white light source and/or a deep-ultraviolet (DUV) laser light source. JP-2008-216790-A discloses a defect inspection apparatus that uses detection optics formed with an oval aperture, to achieve the mounting of a plurality of detection optics having a large numerical aperture (NA). U.S. Pat. No. 6,373,565 discloses a defect inspection apparatus using a mode-locked laser to inspect surface detects. Other related techniques include those disclosed in JP-2003-194739-A, JP-1999-045842-A, JP-2007-142052-A, JP-2011-171521-A, JP-2004-271498-A.

SUMMARY OF THE INVENTION

With finer structuring of circuit patterns during semiconductor-manufacturing processes, physical dimensions of the defects affecting the performance of the semiconductor device are decreasing and a need is arising to detect the defects with higher sensitivity. Optical inspection apparatuses are required to detect the defects of sizes less than one-tenth of the wavelength of the light used for inspection. In this wavelength region, the amount of light scattered from a defect can be approximated using a Rayleigh scattering coefficient, and is proportional to the sixth power of the defect size and inversely proportional to the fourth power of the wavelength.

Accordingly, reduction in the wavelength of the illumination light source to be used for inspection is being demanded. Since the amount of light scattered from a defect is proportional to the amount of illumination light, the enhancement of output is also required of the illumination light source. In addition, detection optics is required to be more accurate (i.e., to spread diffraction performance limits) and larger in NA, for enhanced converging efficiency of the defect-scattered light and thus for image acquisition with higher resolution. Furthermore, arranging a plurality of large NA (numerical aperture) detection optics is needed so that a plurality of kinds of defects different in scattering direction can be detected. Moreover, the improvement of sensitivity is required of sensors to detect very weak light scatterings.

Wavelength conversion using a non-linear optical crystal is used to reduce the wavelength of illumination light. To realize a light source of high output at a short wavelength, it becomes an issue how to construct a wavelength conversion optical system having high wavelength-conversion efficiency and high resistance to input power. Enhancing the NA of detection optics uses a technique for correcting aberration by increasing the number and design flexibility of lenses constituting the detection optics. Increasing the number of lenses, however, tightens requirements relating to permissible surface accuracy or profile irregularity per lens and makes it difficult to achieve necessary processing accuracy. In DUV regions, it is also difficult to reduce chromatic aberration since the types of glass materials that can be used are limited because of the significant dispersion of the glass cubes. Additionally, mounting a plurality of detection optics requires using an oval lens aperture, and it is difficult to realize the lenses whose surface accuracy or profile irregularity requirements can be met even if the lens does not have a rotationally symmetrical shape.

Both the reduction in wavelength and the enhancement of output power are implemented by using a pulse oscillation type of laser that is suitable for generation of high optical output power in a short-wavelength region. In addition, a spectral bandwidth is narrowed down so that the amount of chromatic aberration for detection optics with single glass material (without compensation of the chromatic aberration) is lowered to a permissible level. Using a highly workable glass material to construct the detection optics enables necessary surface accuracy or profile irregularity conditions to be met, even if the number of lenses is increased for larger NA or the lens does not have a rotationally symmetrical shape.

Defect detection sensitivity can be enhanced by realizing a laser light source adapted to generate high output at short wavelengths, and defect detection system with large NA detection optics.

DESCRIPTION OF THE PREFERRED EMBODIMENTS

Hereunder, embodiments of the present invention will be described with reference to the accompanying drawings.
(First Embodiment)

Figure 1:
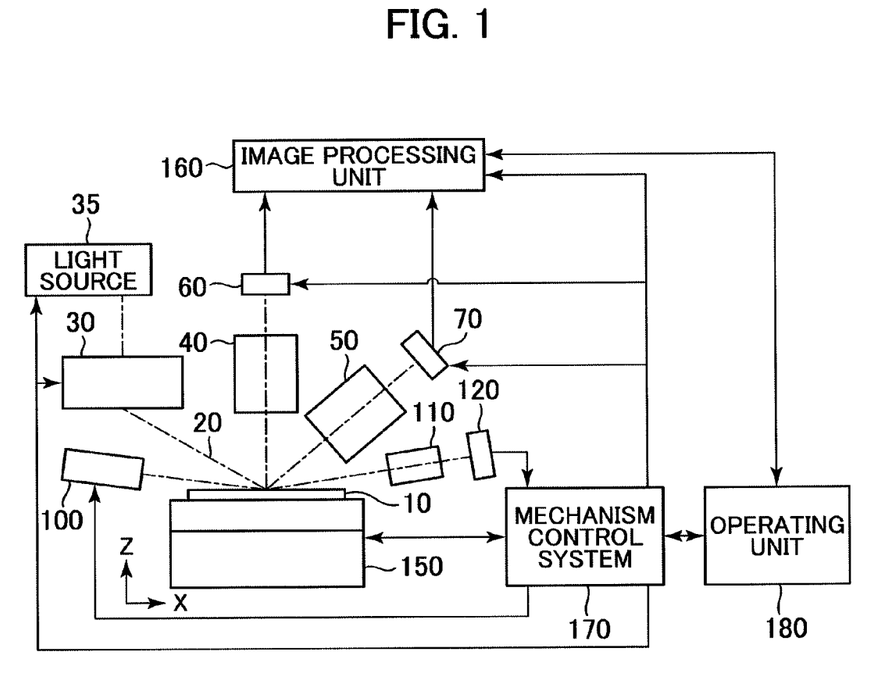
FIG. 1 is a diagram showing a configuration of a defect inspection apparatus according to an embodiment.

FIG. 1 shows an overall configuration of a defect inspection apparatus according to the present embodiment. A sample 10 (such as semiconductor wafer, display element, printed circuit substrate, or the like) that is to be inspected is mounted on a stage 150. The stage 150 is constructed as a combination of, for example, an X-Y stage, a Z-stage, a θ-stage, and other elements. The stage 150 is arranged so that the sample can be scanned in an X-Y plane to allow for inspection of the entire sample surface through detection optics 40 and 50 placed above. The sample 10 has its thin linear surface region illuminated with illumination light 20 that has exited a light source 35 and passed through an illumination optical system 30. Of the light backscattered from patterns, contamination, and/or the like present on the sample, only light incident upon the detection optics 40, 50 placed above the sample is guided to sensors 60 and 70, then undergoes photoelectric conversion, and is sent as an image signal to an image-processing unit 160. The detection optics 40, 50 may each include an analyzer. The sensors 60, 70 may each be a linear CCD, a TDI sensor, or the like. The image-processing unit compares images sent from same adjacent patterns, and detects defects from differences obtained. The present apparatus has an auto-focusing (AF) system. The AF system includes an illumination system 100, a photo detector system 110, and an AF sensor 120, and the AF system detects a change in height (defocusing) of the sample to avoid blurred imaging with the sensor 60, 70 during the scanning of the sample, and feeds back detection results into a mechanism control system 170.

The light source 35 is a pulse oscillation type of laser that operates in wavelength regions of ultraviolet light. This pulse oscillation type of laser desirably uses third harmonics (333 to 367 nm), fourth harmonics (250 to 275 nm), fifth harmonics (200 to 220 nm), or other higher-harmonics with such a fundamental wave as generated by a laser that operates in infrared-light wavelength regions (1,000-1,100 nm), such as a YAG laser. Alternatively, the laser desirably uses second harmonics (200 to 350 nm), third harmonics (200 to 233 nm), or other harmonics with such a fundamental wave as generated by a laser that operates in visible-light wavelength regions (400 to 700 nm). The light source 35 needs at least to be able to generate an ultraviolet-light output power of 0.1 to 5.0 W. Known lasers for ultraviolet-light generation include a continuous wave (CW) laser, but this type has several bottlenecks. For example, these problems are that: since it needs an enhancement cavity to convert wavelengths, this type of laser is complex in structure; in addition to being expensive, it is difficult to maintain stability of the laser light; and wavelength conversion efficiency is also difficult to raise, and thus an output power exceeding 1 W is difficult to achieve.

Figure 2:
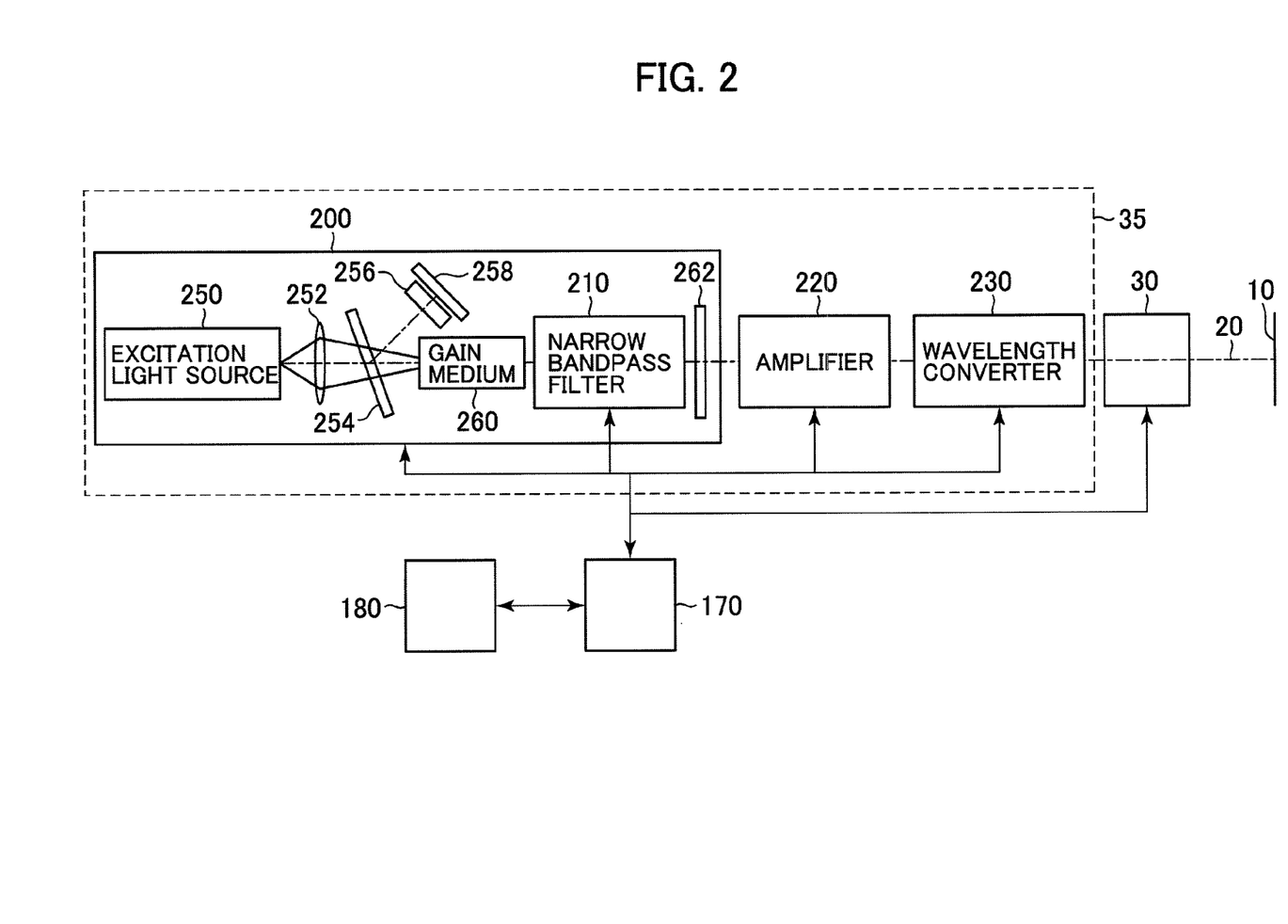
FIG. 2 is a diagram showing an example of a light source used in the defect inspection apparatus according to the embodiment.

FIG. 2 shows an example of configuration of the light source 35. The light source 35 includes a fundamental-wave laser oscillator 200, a narrow band pass filter 210, an amplifier 220, and a wavelength converter 230. A case where a 1-μm wavelength band is used to operate the oscillator is described by way of example below. A mode-locked laser with the narrow band pass filter 210 is used as the oscillator 200. The mode-locked laser is constituted by a resonator fitted with two reflecting elements, 258 and 262, at both ends of the resonator, an excitation light source 250 such as a semiconductor laser, and optics 252 that guides light from the excitation light source 250 into the resonator. As a gain medium 260, a YAG crystal, a YVO crystal, or a fiber doped with Yb or other rare-earth elements is placed inside the resonator consisting of two reflecting elements. Light from the excitation light source 250 is admitted to the gain medium 260 through the optics 252 and whereby light of a wavelength around 1 μm is emitted, and then a saturable absorber, an acousto-optic device or an electro-optic device is used as a mode-locking device 256 to change a cavity loss and hence to generate pulse oscillation.

Figure 4A:
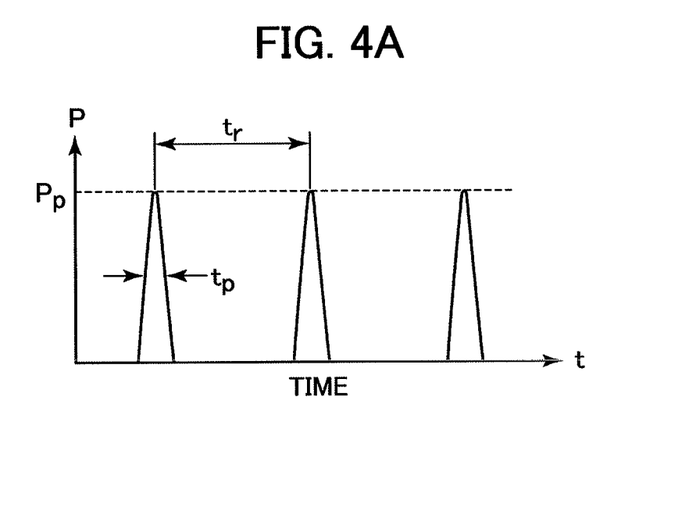
FIGS. 4A and 4B are diagrams showing respectively an example of time dependence of output of a pulse oscillation type of laser, and an example of a related spectrum.
Figure 4B:
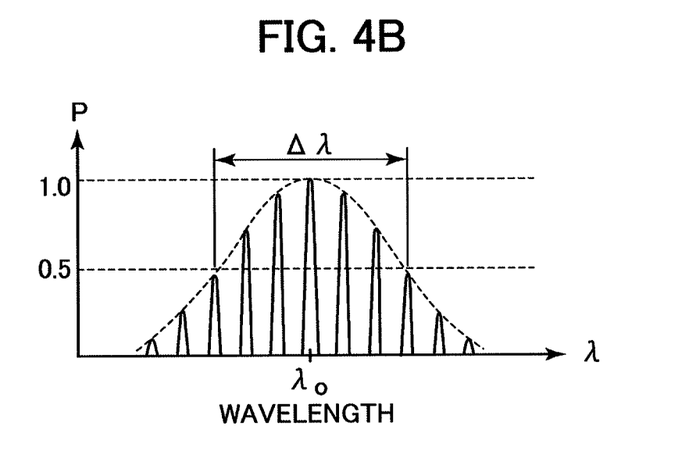
Figure 5:
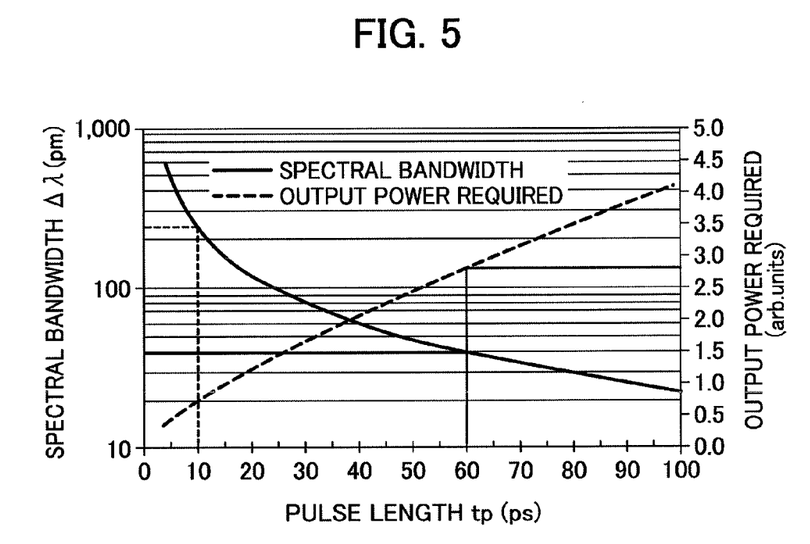
FIG. 5 is a diagram showing an example of dependence of spectral bandwidth and required output power on pulse length in a fundamental wave for the pulse oscillation type laser.

FIGS. 4A and 4B show respectively an example of time dependence of intensity of mode-locked laser light obtained without the narrow band pass filter 210, and an example of a related spectrum. The time dependence of the intensity of the light appear in a form of an equally-pitched continuous pulse train, as shown in FIG. 4A. If length of each pulse is expressed as "$t_p$", and a period of the pulse, as "$t_r$", then a typical value of "$t_p$" and that of "$t_r$" are up to 10 ps and 10 ns, respectively. The spectrum of the light consists of a large number of longitudinal modes, as shown in FIG. 4B. If a central wavelength of the spectrum is expressed as $\Lambda 0$, and a full width at half maximum of the spectrum's envelope, as $\Delta \Lambda$, then a typical value of $\Lambda 0$ and that of $\Delta \Lambda$ are 1,000 to 1,100 nm and up to 240 pm, respectively. FIG. 5 represents a relationship between a Fourier-transform-limited pulse duration and spectral bandwidth of the light. In the present embodiment, the narrow band pass filter 210 for limiting a spectral band of the light is further provided in the resonator. The narrow band pass filter 210 is a birefringent filter, an etalon, or the like. The narrow band pass filter 210 has its transmission band defined so that the spectral bandwidth (full width half maximum) of the light which is output from the laser is in the range between 40 and 100 pm. At this time, as shown in FIG. 5, the length of the pulse takes a value of 30 to 60 ps or greater. The light that the laser oscillator 200 has generated is admitted into the amplifier 220 and after being amplified to nearly 5 to 100 W, further admitted into the wavelength converter 230, and converted into ultraviolet light through two to three levels of wavelength conversion. In the wavelength converter 230, when the n-th harmonic, where n=3 to 5, is generated, the central wavelength of a corresponding spectrum becomes 1/n times and at the same time the spectral bandwidth of the light also becomes 1/n times. After the wavelength conversion, the spectral bandwidth (full width at half maximum) of the light which has been output from the laser provided with the narrow band pass filter 210, therefore, becomes nearly 10 to 20 pm, which is 1/n times that of the fundamental wave. In the present embodiment, the spectral bandwidth of the laser light used to illuminate the sample 10 falls within a light spectral bandwidth that makes permissible at least chromatic aberration of the detection optics 40, 50 described later herein. Thus, large NA detection optics can be realized.

Figure 3:
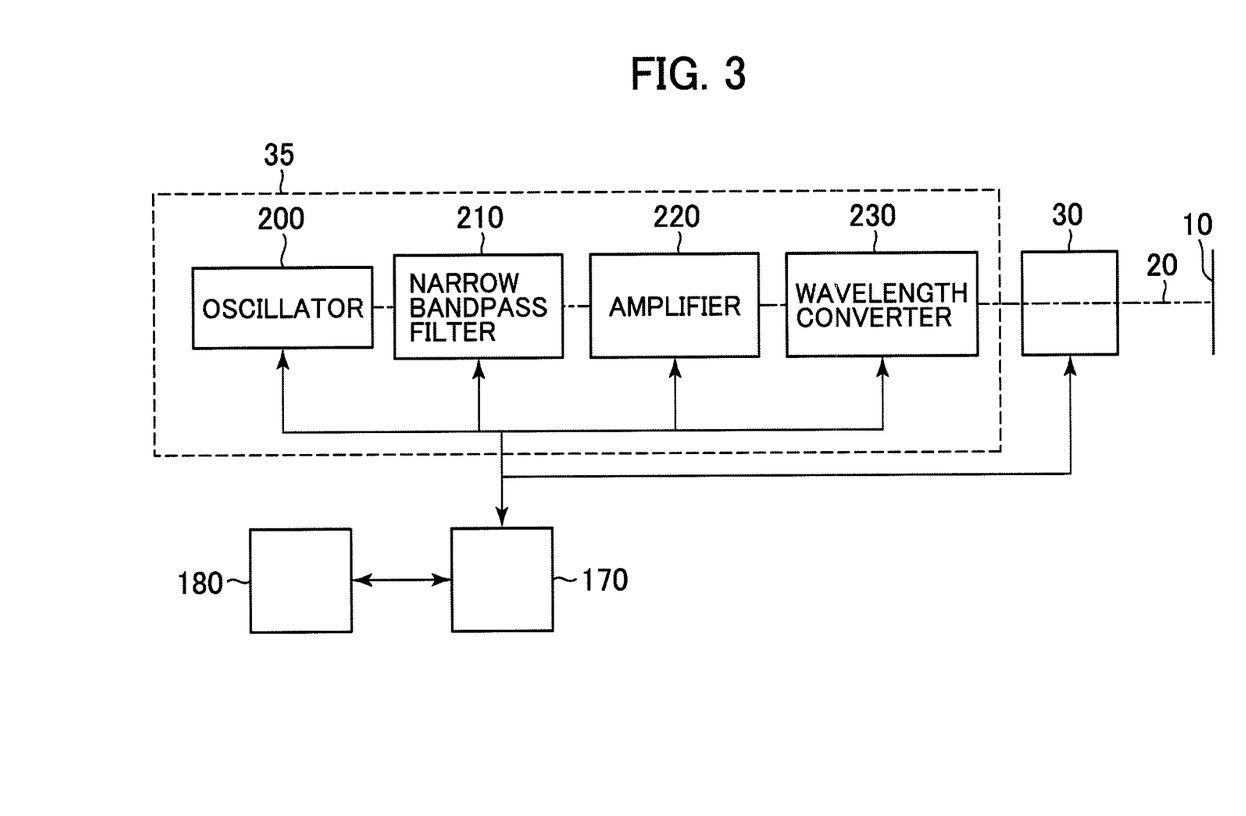
FIG. 3 is a diagram showing another example of a light source.

While the mode-locking element 256 and the reflecting element 258 of the resonator are shown as separate elements in FIG. 2 of the present embodiment, the inspection apparatus may instead use a saturable absorber mirror that has integrated functions of the two elements. Additionally, although the example of placing the narrow band pass filter 210 in the resonator has been shown, this filter may be disposed outside (at rear) of the resonator, as shown in FIG. 3. If the filter 210 is to be placed at the rear of the resonator, an etalon would preferably be used as the filter 210.

In FIG. 2, the narrow band pass filter 210 is placed in the resonator, whereas in FIG. 3, the narrow band pass filter 210 is placed on an optical path present between the oscillator 200 and the amplifier 220, this optical path may also be expressed as one anterior to the amplifier 220, though. Since power density of unamplified light is lower than that of amplified light, placing the narrow band pass filter 210 on the optical path anterior to the amplifier 220 makes the narrow band pass filter 210 longer-lived than placing the narrow band pass filter 210 on an optical path posterior to the amplifier 220.

Additionally, referring to FIGS. 2 and 3, the narrow band pass filter 210 is disposed on an optical path of the fundamental wave, this optical path may also be expressed as one anterior to the wavelength converter 230, though. Optical elements suffer more significant deterioration with light of shorter wavelengths than with light of longer wavelengths. Since the light before undergoing wavelength conversion has a longer wavelength than after undergoing the wavelength conversion, placing the narrow band pass filter 210 on the optical path anterior to the wavelength converter 230 makes the narrow band pass filter 210 longer-lived than placing the narrow band pass filter 210 on an optical path posterior to the wavelength converter 230.

As heretofore set forth, providing the narrow band pass filter 210 to narrow down the band of the illumination light 20 enables the realization of large NA detection optics, whereas resulting extension of the pulse length as shown in FIG. 5 leads to a decrease in wavelength conversion efficiency due to a decrease in peak power and renders the ultraviolet light difficult to enhance in output power. The following describes an example of obtaining frequency-quadrupled waves using two levels of wavelength conversion with infrared light as a fundamental wave.

When wavelength conversion is repeated twice to generate ultraviolet light from the fundamental wave of pulse-oscillating infrared light, all of the fundamental wave of the infrared light, frequency-doubled waves, or visible light obtained after the first wavelength conversion, and frequency-quadrupled waves, or ultraviolet light obtained after the second wavelength conversion, exhibit the time-varying waveforms and spectrum shown in FIGS. 4A, 4B. Expressions 1 and 2 shown below can be used to represent average power values of the respective wavelengths in terms of Pa_IR, Pa_Vis, and Pa_UV, and peak power values in terms of Pp_IR, Pp_Vis, and Pp_UV.

$$Pa\_IR = Pp\_IR \times t_p/t_r \quad \text{[Expression 1]}$$

$$Pa\_UV = Pp\_UV \times t_p/t_r \quad \text{[Expression 2]}$$

Since ultraviolet light arises from a nonlinear effect, an actual pulse length of the fundamental wave becomes shorter than the pulse length ($t_p$) of the fundamental wave. However, it has been presupposed here that the former of the two pulse lengths remains invariant.

If the conversion efficiency for obtaining frequency-doubled waves is taken as "e1", and the conversion efficiency for obtaining frequency-quadrupled waves is taken as "e2", since visible light of the frequency-doubled waves results from the nonlinear effect, the corresponding conversion efficiency "e1" can be represented as follows using expression 3:

$$e1 \propto Pp\_IR = Pa\_IR \times t_r/t_p \quad \text{[Expression 3]}$$

Accordingly the peak power Pp_Vis of the visible light of the frequency-doubled waves can be represented as follows using expression 4:

$$Pp\_Vis = e1 \times Pp\_IR \propto Pp\_IR^2 = (Pa\_IR \times t_r/t_p)^2 \quad \text{[Expression 4]}$$

Before the ultraviolet light of the frequency-quadrupled waves can be obtained, this light needs to go through one more level of wavelength conversion. In other words, expression 6 in addition to expression 5 needs to be used before the ultraviolet light can be represented.

$$e2 \propto Pp\_Vis \quad \text{[Expression 5]}$$

$$Pp\_UV = e2 \times Pp\_Vis \propto Pp\_Vis^2 = Pp\_IR^4 = (Pa\_IR \times t_r/t_p)^4 \quad \text{[Expression 6]}$$

Following expression 7 can be derived from expressions 2 and 6:

$$Pa\_UV \propto (Pa\_IR \times t_r/t_p)^4 \times t_p/t_r = Pa\_IR^4 \times (t_r/t_p)^3 \quad \text{[Expression 7]}$$

Therefore, the average power Pa_IR of the fundamental wave that is needed to keep the average power Pa_UV of the ultraviolet light when the pulse length and the pulse period change can be represented as follows using expression 8:

$$Pa\_IR \propto (Pa\_UV \times (t_p/t_r)^3)^{1/4} \quad \text{[Expression 8]}$$

It can be seen from expression 8 that when a period between the pulses "$t_r$" is constant, the fundamental wave requires greater power with increasing pulse length "$t_p$". This relationship is shown, along with the spectral bandwidth of the light, in a graph of FIG. 5. The graph indicates that as the spectral bandwidth of the illumination light 20 is narrowed for the realization of large NA detection optics, the pulse length increases, which in turn increases the fundamental wave power required for obtaining the high ultraviolet-light power necessary to enhance sensitivity, and that the increase in the fundamental wave power works as a restriction relating to the enhancement of the ultraviolet-light output power of the light source. For this reason, the light source desirably has the maximum spectral bandwidth of the light as long as large NA detection optics can be realized.

More specifically, to generate ultraviolet light from the fundamental wave of the pulse-oscillating infrared light by repeating wavelength conversion twice, the light spectral bandwidth of the fundamental wave is preferably changed to nearly 40 to 100 pm and the spectral bandwidth of the ultraviolet light to nearly 10 to 20 pm. The pulse length at this time is no more than nearly 25 to 50 ps. The power of the fundamental wave that is needed to obtain the predetermined power of the ultraviolet light is no more than four times that of conventional laser light having a pulse length of around 10 ps, and this power level falls in an achievable range.

Figure 6:
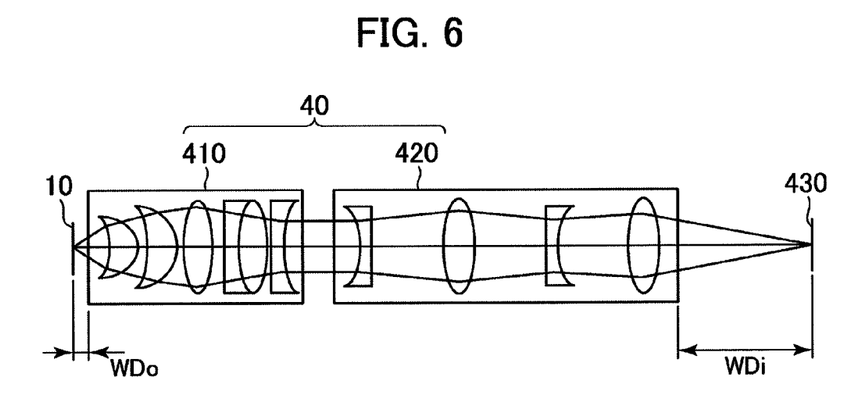
FIG. 6 is a diagram showing detection optics of the defect inspection apparatus according to the embodiment.

A projection lens with an NA of nearly 0.4 to 0.9 is used for the detection optics 40, 50. Through this lens, a region that measures nearly 0.5 to 2.0 mm long by 1.0 μm wide on the surface of the sample 10 is imaged on a photo detection surface of the sensor 60, 70, with performance approximate to the diffraction-limit. A projection magnification is about 20 to 50 times. A working distance of approximately 5 to 10 mm needs to be allowed at the sample side to irradiate the sample with the illumination light 20. A schematic configuration of the detection optics 40 is shown in FIG. 6. The detection optics 40 includes a front group 410 and a rear group 420. The front group 410 has an NA of nearly 0.4 to 0.9 at the sample 10 side and acquires scattered light from the surface of the sample 10. The rear group 420 guides the light from the front group 410 to an image plane 430 and forms an image of the surface of the sample 10 on the image plane 430.

If the front group 410 is designed to be a Fourier transform lens with a Fourier plane positioned between the front group 410 and the rear group 420, this enables spatial filtering for removing unnecessary diffracted light from the Fourier plane. If any diffracted light from patterns formed on the surface of the sample 10 is removed by a spatial filter, therefore, highly sensitive detection of contamination and pattern defects (abnormality of the patterns) can be implemented without a pattern detection error.

In addition, if the rear group 420 is formed as a zoom lens, the image of the sample surface that is acquired by the sensor 60 can be changed in pixel size on the surface of the sample 10. This means changing a sampling period (or pitch) of images and a visual field of imaging, and thus allows an appropriate action to be taken according to requirements. For example, highly fine images can be acquired by reducing the sampling period (or pitch), or images can be acquired more rapidly by increasing the sampling period (or pitch), that is, spreading the imaging field.

The front group 410 and rear group 420 constituting the detection optics 40 are composed of a plurality of lenses formed from synthetic silica adapted to ultraviolet light. High resistance of the synthetic silica to ultraviolet light makes the silica difficult to deteriorate. In addition to these features, excellent workability of the synthetic silica enables individual lenses to be surface-finished with high surface accuracy, and thus a transmitted-wavefront aberration of the entire lens to be controlled below a diffraction-limit of 0.07 Λrms.

Figure 12:
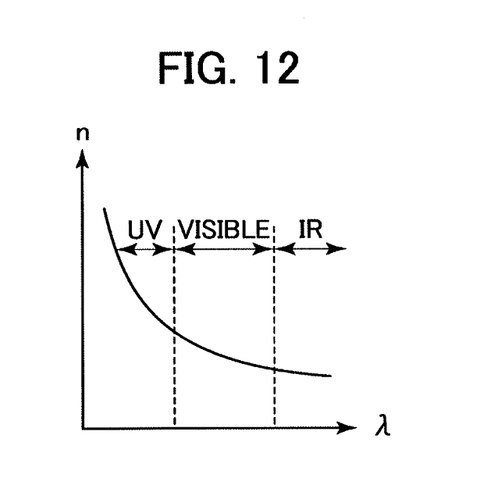
FIG. 12 is a diagram showing an example of wavelength dependence of a refractive index of a glass material used in the detection optics.

Meanwhile, if the lens is formed only from synthetic silica, chromatic aberration may become a problem, particularly when the spectral line width of the light from the light source is not sufficiently small. An example of wavelength dependence of a refractive index of a glass material such as synthetic silica is shown in FIG. 12. This figure indicates that while the refractive index increases with decreasing wavelength, this rate of change rises at shorter wavelengths and in ultraviolet regions, generates more significant chromatic aberration than that of visible light. In addition, chromatic aberration varies as the second power of the NA of the lens, and is thus particularly influential when the NA is large.

Figure 7A:
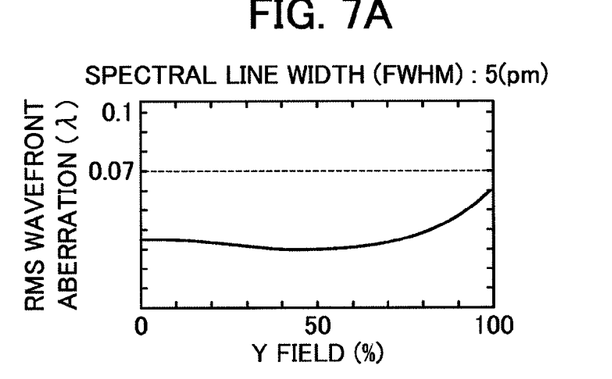
FIGS. 7A, 7B, and 7C are diagrams that show spectral bandwidth dependence of aberration characteristics of the detection optics in the defect inspection apparatus according to the embodiment.
Figure 7B:
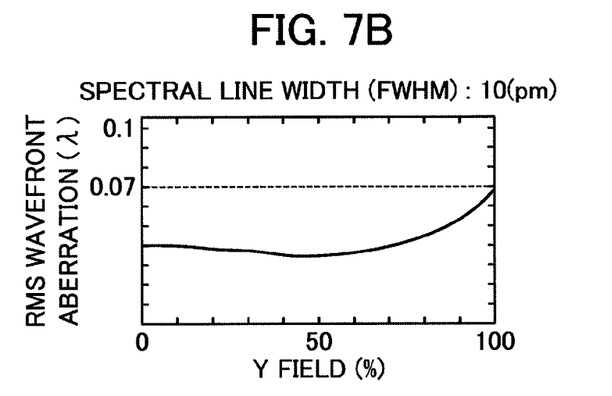
Figure 7C:
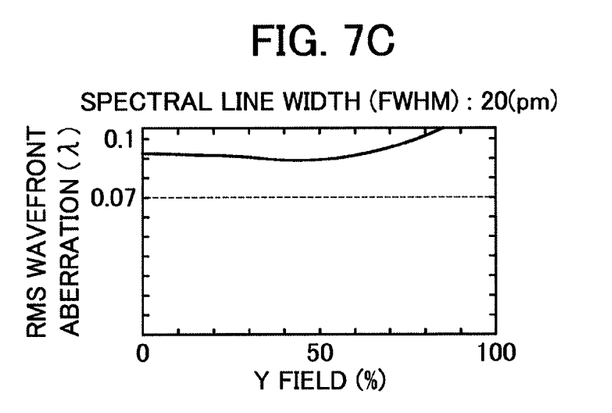

FIGS. 7A, 7B, and 7C show calculation results on object height (Y) dependence of the wavefront aberration in typical detection optics, these calculation results being shown independently for each of three cases in which the spectral line width (FWHM) of the light source is 5 pm (FIG. 7A), 10 pm (FIG. 7B), and 20 pm (FIG. 7C). At the line widths of 5 pm and 10 pm, the wavefront aberration is controlled below the diffraction-limit of 0.07 λrms, whereas at the line width of 20 pm, performance lacks by nearly 0.1 Λrms. In the present embodiment, in addition to the fact that the detection optics is formed from synthetic silica, the pulse oscillation type of laser whose spectral line width is reduced below 10 pm is used as the light source. Thanks to these characteristics, chromatic aberration is controlled to a level at which it does not become a problem.

In a first alternative method, the detection optics may be formed by combining a plurality of glass materials, such as synthetic silica and calcium fluoride, to reduce chromatic aberration, and an existing pulse oscillation type of laser with a spectral line width exceeding 10 pm may be used as the light source. Fluorite is a glass material that has low workability into detection optics and is expensive. The use of this material in the first alternative method, therefore, increases a manufacturing cost in addition to making surface accuracy difficult to obtain, but allows reduction in chromatic aberration.

In a second alternative method, the detection optics may be formed from synthetic silica, and a continuous oscillation type of laser with a spectral line width less than 1 pm may be used as the light source. The continuous oscillation type of laser is complex in structure, which makes it difficult to maintain stability of light and leads to an increase in manufacturing cost. In addition, the laser itself is unsuitable for use as a light source of high output power. However, this laser can reduce chromatic aberration.

The configurational and other effectiveness of the inspection apparatus have been described taking the use of the detection optics 40 as an example in the present embodiment, and the same also applies to using the detection optics 50.

Providing a plurality of detection optics, for example the plural detection optics 40 and 50 as shown in FIG. 1, could cause mechanical interference between them to become a problem. If defect detection sensitivity is enhanced too much, that problem, in particular, will manifest itself since a need will arise to increase the NA of the detection optics.

Figures 8A, 8B:
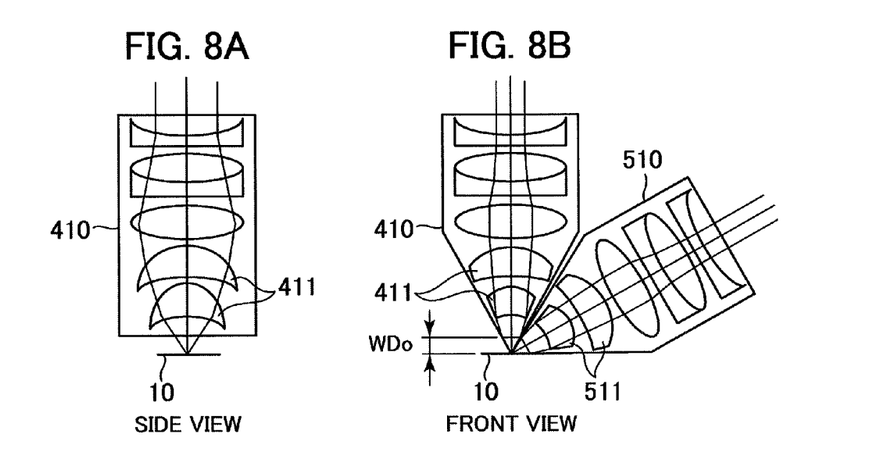
FIGS. 8A and 8B are diagrams that show layout of a front group of the detection optics in the defect inspection apparatus according to the embodiment.
Figure 8C:
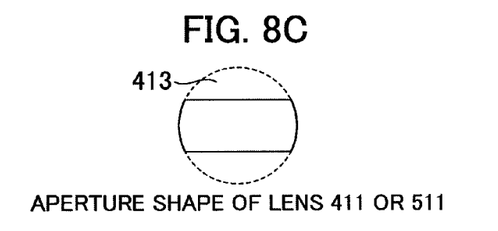
FIG. 8C is a diagram showing an aperture shape of the front group.

In contrast to this, the present embodiment is configured so that as shown in FIGS. 8A, 8B, and 8C, a portion at which the plural detection optics interfere with each other and a portion at which each detection optics interferes with the surface of the sample 10 are cut off to form an elliptical or any other non-round aperture such as that shown in FIG. 8C, thereby an effective aperture size being maximized. FIGS. 8A, 8B show the front groups 410 and 510 existing as partially extracted from the detection optics 40 and 50. In FIG. 8A, which is a side view of the detection optics 40, a maximum achievable aperture size of nearly NA=0.6 to 0.9 is ensured, whereas in FIG. 8B, which is a front view of the detection optics 40 and 50, an aperture size of nearly NA=0.3 to 0.5 is obtained by cutting off either the portion at which one detection optics interferes with the other adjacent detection optics, or the portion at which the detection optics interferes with the surface of the sample 10. In other words, at least one of the plural detection optics 40 and 50 in the present embodiment differs in NA at two sections passing through an optical axis and orthogonal to each other.

Of the lenses constituting the front group 410 or 510, an outline of at least a lens 411 or 511 close to the object that is the sample 10 needs to be formed into a shape obtained by cutting off a portion 413 of a circle, as shown in FIG. 8C. It is not easy to ensure necessary lens performance while maintaining this shape obtained by cutting off one portion of the circle. In particular, to correct chromatic aberration using fluorite or any other low-workability (brittle) glass material, it is desirable that attention be paid to ensuring accuracy. Accordingly, the present embodiment does not use fluorite or the like. Instead, only synthetic silica, a glass material of high workability, is used to constitute the detection optics 40, 50. This enables wavefront aberration accuracy of a diffraction-limit level to be obtained using the lens of a shape obtained by cutting off a portion of a circle.

Figure 9:
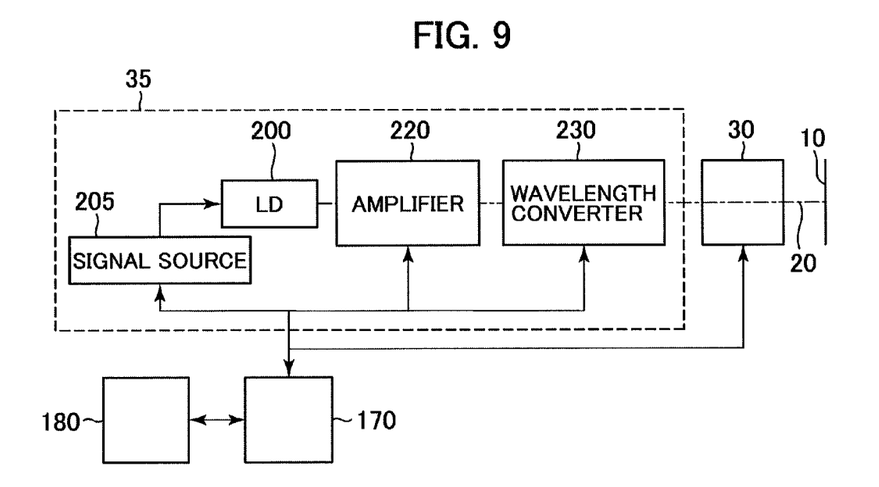
FIG. 9 is a diagram showing yet another example of a light source.

FIG. 9 shows yet another example of a light source used in the defect inspection apparatus of the present embodiment. The light source 35, a semiconductor laser as a laser oscillator 200 that generates a fundamental wave, includes a signal source 205 that generates a pulse signal to drive the laser. The light source 35 also includes an amplifier 220 and a wavelength converter 230. A wavelength band that the laser oscillator 200 can use to generate oscillations is, for example, 1 μm, 800 to 900 nm, 600 to 700 nm, 400 to 450 nm, and so forth. Any other waveform band may be applied, only if it enables easy semiconductor laser oscillation.

Figure 10A:
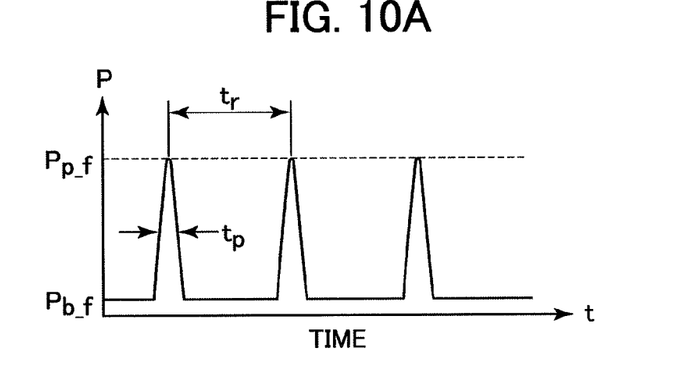
FIGS. 10A, 10B, and 10C are diagrams showing other examples of time dependence of output and spectra of the light source.
Figure 11:
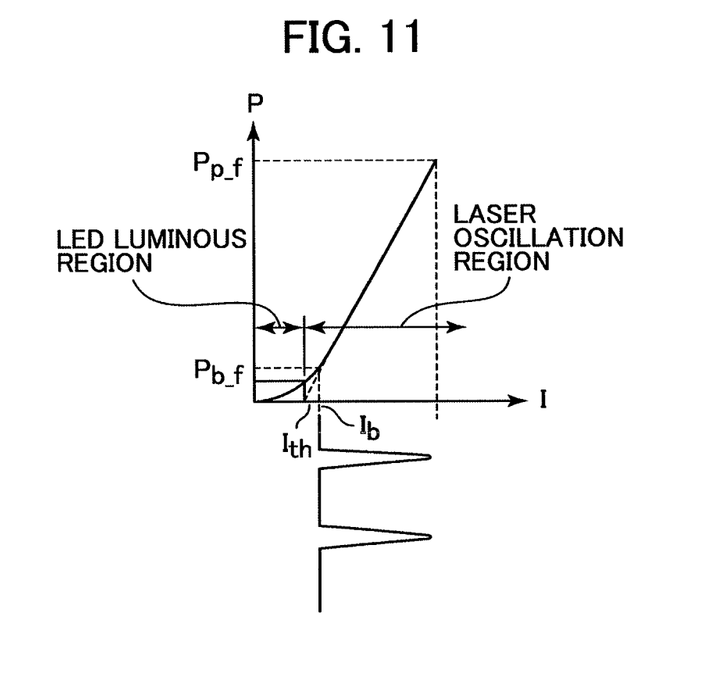
FIG. 11 is a diagram representing a relationship between an electric current and optical output of a semiconductor laser.

A signal of, for example, 10 ps in pulse length and 10 ns in pulse period, is generated from the signal source, then when this signal is supplied to the semiconductor laser, an offset (Ib shown in FIG. 11) that is needed to maintain lasing is added to the offset, and the semiconductor laser is driven to generate pulse oscillations in a waveform shown in FIG. 10A. FIG. 11 shows a relationship between a driving current and optical output of the semiconductor laser. As shown in FIG. 11, when the current is at its threshold level (Ith) or less, no laser oscillation and light is composed mainly of LED light components, but once the threshold level has been exceeded, laser oscillation does occur.

For this reason, an offset current exceeding the threshold level is continuously supplied during a pulse-to-pulse period to maintain laser oscillation. Always maintaining the oscillation state of the laser allows a correlation in phase between individual light pulses to be maintained and a spectrum of the light to be prevented from spreading more than necessary.

Figure 10B:
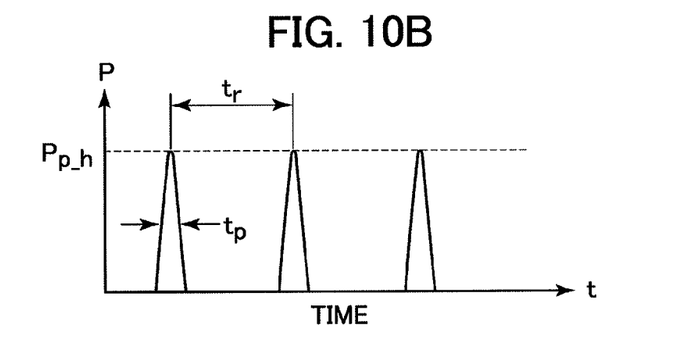
Figure 10C:
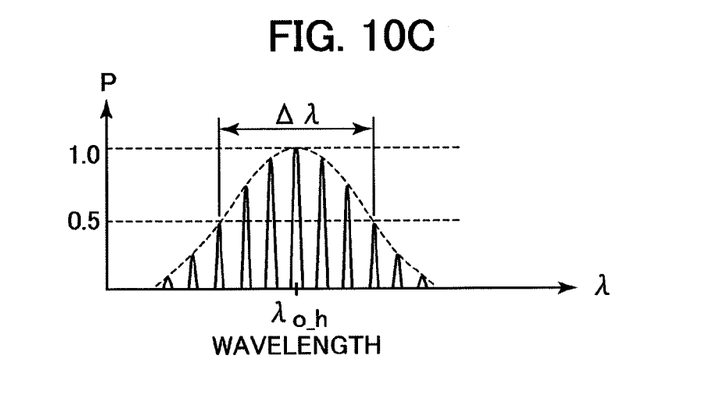

The spectrum of the laser output light thus obtained will take a distribution shown in FIG. 10C, and a relationship between the pulse length and spectral bandwidth of the light will appear as shown in FIG. 5. In the present example, since the spectral bandwidth of the light can be controlled by varying the pulse length, a spectral bandwidth of the light of 40 to 100 pm can be set by, instead of using the narrow band pass filter, setting a value of 30 to 60 ps as the length of the pulses which the signal source 205 is to generate. The amplifier 220 amplifies the thus-obtained pulse oscillation light of a narrow band and then the wavelength converter 230 converts the light into higher harmonic waves (frequency-doubled to frequency-quadrupled waves) to obtain ultraviolet light.

Because of low light emission intensity between pulses, sufficient conversion efficiency would not be obtainable when the wavelength converter 230 conducts the wavelength conversion. The harmonics output after the wavelength conversion, therefore, will have a pulse-shaped waveform as shown in FIG. 10B. In the present example, although the signal source 205 is needed to generate high-frequency signals, a simplified configuration of the laser oscillator 200 which generates the fundamental wave offers advantages in stability and cost.

The semiconductor laser may be driven only with the pulse signal, instead of adding the offset component to the driving signal of the laser. In that case, while the correlation in phase between the light pulses decreases and thus the spectrum of the light is likely to spread, this can be compensated for by extending the pulse length.

It is to be noted that the present invention is not limited to the aforementioned embodiments, but covers various modifications. While, for illustrative purposes, those embodiments have been described specifically, the present invention is not necessarily limited to the specific forms disclosed. Thus, partial replacement is possible between the components of a certain embodiment and the components of another. Likewise, certain components can be added to or removed from the embodiments disclosed.

What is claimed is:

1. A defect inspection apparatus comprising:
a pulsed laser light source for emitting ultraviolet light;
illumination optics for irradiating with the ultraviolet light a surface of a sample;
first detection optics for forming a first enlarged image of the surface of the sample;
an image sensor for detecting light back-scattered on the surface of the sample to acquire the first enlarged image of the sample; and
an image processing unit for processing the first enlarged image of the sample;
wherein:
the pulsed laser light source comprises:
a mode-locked laser as an oscillator;
a band pass filter for narrowing a spectral bandwidth of light from the mode-locked laser;
an amplifier disposed posterior to the band pass filter; and
a wavelength converter configured to convert light amplified by the amplifier into the ultraviolet light;
the spectral bandwidth of the light narrowed down by the band pass filter falls within a light-spectral bandwidth range permissible according to a particular chromatic aberration level of the illumination optics and a particular chromatic aberration level of the first detection optics; and
the spectral bandwidth of the ultraviolet light output from the pulsed laser light source is between 10 pm and 20 pm.

2. The defect inspection apparatus according to claim 1, wherein:
the first detection optics uses only synthetic silica as a glass material.

3. The defect inspection apparatus according to claim 2, wherein:
a lens with rotationally asymmetric aperture is used for the first detection optics.

4. The defect inspection apparatus according to claim 1, wherein:
a lens whose numerical aperture at the sample side exceeds 0.5 is used for the first detection optics.

5. The defect inspection apparatus according to claim 1, wherein:
the pulsed laser light source is a laser which uses pulse-driven semiconductor laser light as a fundamental wave.

6. A defect inspection method comprising:
emitting light from a mode-locked laser as an oscillator;
narrowing a spectral bandwidth of the light from the mode-locked laser by a band pass filter;
amplifying the light from the band pass filter by an amplifier disposed posterior to the band pass filter;
converting the light amplified by the amplifier into ultraviolet light by a wavelength converter;

emitting the ultraviolet light of a narrowed wavelength from a pulsed laser light source;

using illumination optics to irradiate with the ultraviolet light a surface of a sample;

using first detection optics to form a first enlarged image of the surface of the sample;

acquiring the first enlarged image via an image sensor by detecting light back-scattered on the surface of the sample, and after processing of the first enlarged image, detecting defects on the sample; and controlling a spectral bandwidth of the light narrowed down by the band pass filter to fall within a light-spectral bandwidth range permissible according to a particular chromatic aberration level of the illumination optics and a particular chromatic aberration level of the first detection optics;

wherein the spectral bandwidth of the ultraviolet light output from the pulsed laser light source is between 10 pm and 20 pm.

7. The defect inspection apparatus according to claim 1, further comprising:

second detection optics for forming a second enlarged image of the surface of the sample; wherein:

the first detection optics detects first light scattered at first scattering angle range, the second detection optics detects second light scattered at second scattering angle range which is different from the first scattering angle range, and the spectral bandwidth falls within the light-spectral bandwidth range permissible according to the particular chromatic aberration level of the illumination optics, the particular chromatic aberration level of the first detection optics, and a particular chromatic aberration level of the second detection optics.

* * * * *